United States Patent
Kern et al.

(10) Patent No.: US 10,407,305 B2
(45) Date of Patent: Sep. 10, 2019

(54) APPARATUS AND PROCESS FOR PREPARING ACETYLENE AND SYNTHESIS GAS

(71) Applicant: BASF SE, Ludwigshafen (DE)

(72) Inventors: Matthias Kern, Deidesheim (DE); Michael Russ, Roemerberg (DE); Peter Renze, Mannheim (DE); Maximilian Vicari, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 351 days.

(21) Appl. No.: 14/912,809

(22) PCT Filed: Aug. 28, 2014

(86) PCT No.: PCT/EP2014/068235
§ 371 (c)(1),
(2) Date: Feb. 18, 2016

(87) PCT Pub. No.: WO2015/028540
PCT Pub. Date: Mar. 5, 2015

(65) Prior Publication Data
US 2016/0207767 A1  Jul. 21, 2016

(30) Foreign Application Priority Data

Aug. 29, 2013 (EP) .................................. 13182228

(51) Int. Cl.
*C01B 3/36* (2006.01)
*B01J 19/24* (2006.01)
(Continued)

(52) U.S. Cl.
CPC ................. *C01B 3/36* (2013.01); *B01J 4/002* (2013.01); *B01J 19/24* (2013.01); *C07C 2/78* (2013.01);
(Continued)

(58) Field of Classification Search
CPC .. C01B 3/36; B01J 4/002; B01J 19/24; C07C 2/78
(Continued)

(56) References Cited

U.S. PATENT DOCUMENTS 541,781 A * 6/1895 Wheeler ............... B01F 5/0428
 261/76
3,396,207 A 8/1968 Bartholomé et al.
(Continued)

FOREIGN PATENT DOCUMENTS

DE  875 198 C  4/1953
DE  1 051 845 B  3/1959
(Continued)

OTHER PUBLICATIONS

"Correlation of Swirl Number for a Radial-Type Swirl Generator", H. J. Sheen et al., Institute of Applied Mechanics, National Taiwan Unitiversity, Taipei 10764, Taiwan—1996.*
(Continued)

*Primary Examiner* — Huy Tram Nguyen
(74) *Attorney, Agent, or Firm* — Oblon, McClelland, Maier & Neustadt, L.L.P.

(57) ABSTRACT

An apparatus (10) for preparing acetylene and synthesis gas by partial oxidation of hydrocarbons with oxygen is proposed, comprising a mixing unit (12), a mixing section and a mixing diffuser (16). The mixing unit (12) has a feed orifice (18) for supply of a hydrocarbonaceous stream, a feed orifice (20) for supply of an oxygenous stream, a swirl register and a distributor plate (24). The distributor plate (24) is disposed between the mixing section (14) and the feed orifice (18) for supply of a hydrocarbonaceous stream. The distributor plate (24) has orifices (28). The swirl register (22) is disposed between the feed orifice (20) for supply of an oxygenous stream and the mixing section (14). The mixing diffuser (16) is connected to the mixing section (14).

(Continued)

Figure 1:
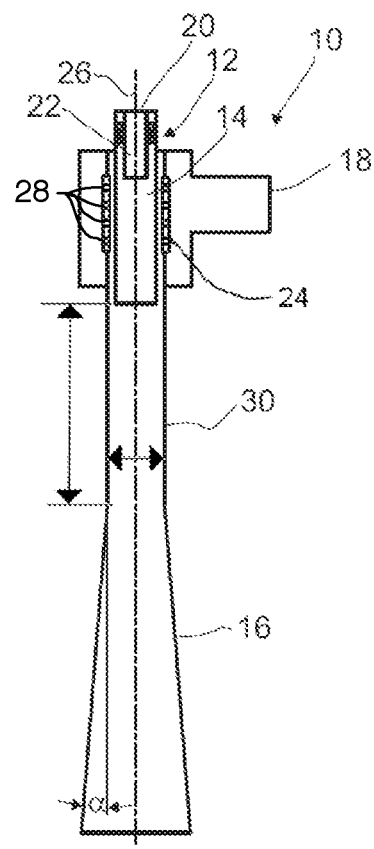

There is a further proposal of a process for preparing acetylene and synthesis gas by partial oxidation of hydrocarbons with oxygen.

14 Claims, 2 Drawing Sheets

(51) Int. Cl.
  *C07C 2/78* (2006.01)
  *B01J 4/00* (2006.01)
(52) U.S. Cl.
  CPC ... *B01J 2219/24* (2013.01); *C01B 2203/0255* (2013.01); *C01B 2203/062* (2013.01); *C01B 2203/1235* (2013.01)
(58) Field of Classification Search
  USPC ............................................ 422/224
  See application file for complete search history.

(56) References Cited

U.S. PATENT DOCUMENTS

| | | | | |
|---|---|---|---|---|
| 3,980,233 | A * | 9/1976 | Simmons | F23D 11/107 239/400 |
| 4,203,718 | A * | 5/1980 | Tracy | F23C 7/008 239/407 |
| 4,443,182 | A * | 4/1984 | Wojcieson | F23C 7/00 239/406 |
| 5,092,981 | A * | 3/1992 | Russo | C10G 9/002 208/130 |
| 5,789,644 | A * | 8/1998 | Passler | B01J 4/001 252/373 |
| 6,210,123 | B1 * | 4/2001 | Wittrisch | F04F 5/466 417/194 |
| 8,196,845 | B2 * | 6/2012 | Thomson | F23D 11/107 239/132 |
| 8,517,719 | B2 * | 8/2013 | Briggs, Jr. | F23C 7/006 431/182 |
| 2007/0151154 | A1 * | 7/2007 | Lyubovsky | B01F 3/04049 48/197 R |
| 2008/0134580 | A1 | 6/2008 | Kah et al. | |
| 2008/0188698 | A1 | 8/2008 | Bartenbach et al. | |
| 2013/0032639 | A1 * | 2/2013 | Harding | F23R 3/28 239/8 |
| 2013/0058835 | A1 * | 3/2013 | Salazar-Guillen | B01J 19/26 422/129 |
| 2013/0153074 | A1 * | 6/2013 | Gurr | F15D 1/06 138/39 |

FOREIGN PATENT DOCUMENTS

| | | |
|---|---|---|
| DE | 1 057 094 B | 5/1959 |
| DE | 44 22 815 A1 | 1/1996 |
| DE | 10 2005 001 900 A1 | 7/2006 |
| DE | 10 2005 018 981 A1 | 10/2006 |

OTHER PUBLICATIONS

International Search Report dated Oct. 22, 2014 in PCT/EP2014/068235.
International Preliminary Report of Patentability dated Mar. 3, 2016 in PCT/EP2014/068235 (English translation only).

* cited by examiner

APPARATUS AND PROCESS FOR PREPARING ACETYLENE AND SYNTHESIS GAS

The present invention relates to an improved apparatus and to an improved process for preparing acetylene and synthesis gas by partial oxidation of hydrocarbons in a reactor, in which a stream comprising the hydrocarbon and a stream comprising the oxygen are fed to the reactor.

High-temperature reactions for partial oxidation of hydrocarbons are typically conducted in a reactor system composed of mixing unit, burner block, firing space and quench device. One example of such a partial oxidation in the high-temperature range is the preparation of acetylene and synthesis gas by partial oxidation of hydrocarbons. This is described, for example, in DE 875198, DE 1051845, DE 1057094 and DE 4422815.

These documents elucidate the mixer/burner block/firing space/quench combinations typically used for the BASF-Sachsse-Bartholomé acetylene process—referred to hereinafter, when the combination is being referred to, simply as "reactor".

In this process, the starting materials, for example natural gas and oxygen, are heated separately, typically up to 600° C. In a mixing zone, the reactants are mixed intensively, flow through a burner block and then are reacted exothermically in a firing space. In these cases, the burner block consists of a particular number of parallel channels in which the flow velocity of the ignitable oxygen/natural gas mixture is higher than the flame velocity (reaction rate, conversion rate), in order to prevent the flame from penetrating into the mixing space. The metallic burner block is cooled in order to withstand the thermal stresses. According to the residence time in the mixing space, the risk arises of premature ignition and reignition owing to the limited thermal stability of the mixtures. The term "ignition delay time" or "induction time" is used here to mean that period within which an ignitable mixture does not undergo any significant intrinsic thermal alteration. The induction time depends on the type of hydrocarbons used, the mixing state, pressure and temperature. It determines the maximum residence time of the reactants in the mixing space. Reactants such as hydrogen, liquefied gas or light petroleum, the use of which is particularly desirable owing to enhanced yield and/or capacity in the synthesis process, are notable for a comparatively high reactivity and hence short induction time.

In spite of the advantages achieved by these apparatuses, there is still potential for improvement. For instance, in the Sachsse-Bartholomé acetylene synthesis, complete mixing of the reactant streams is important. In this context, in the known apparatuses, there can be an unintentional hydrodynamic pressure surge. Especially at high throughputs, this limits the capacity of the plant, since a rise in yield can be achieved only by a pressure increase. In addition, asymmetric flow toward a mixing-optimized swirl register can result in maldistribution of the reactant concentration and the mass flow density in the mixing device, which leads to a reduction in the yield in the downstream reactor.

It is therefore an object of the present invention to give an apparatus and a process which at least substantially reduces the above-described disadvantages and especially avoids possible maldistributions downstream of the swirl register.

A basic idea of the present invention is to avoid a possible maldistribution downstream of the swirl register through a suitable design of the swirl register, which can be specified via what is called the swirl number and the type and alignment of the swirl-generating deflection plates. The inventive design of the swirl register and of the cross section of the mixing device can avoid an unintentional hydrodynamic pressure surge in the mixing device. This can likewise be specified via the characteristic parameters of swirl number and Reynolds number.

An inventive apparatus for preparing acetylene and synthesis gas by partial oxidation of hydrocarbons with oxygen comprises a mixing unit, a mixing section and a mixing diffuser. The mixing unit has a feed orifice for supply of a hydrocarbonaceous stream, a feed orifice for supply of an oxygenous stream, a swirl register and a distributor plate. The distributor plate is disposed between the mixing section and the feed orifice for supply of a hydrocarbonaceous stream. The distributor plate has orifices. The swirl register is disposed between the feed orifice for supply of an oxygenous stream and the mixing section. The mixing diffuser is connected to the mixing section.

The mixing section may be essentially cylindrical. The distributor plate may be configured such that the distributor plate completely surrounds the mixing section, viewed in a circumferential direction. The swirl register may be disposed at least partly within the distributor plate. The distributor plate may have orifices for distribution of the hydrocarbonaceous stream. The orifices may preferably be arranged in homogeneous distribution in the distributor plate. Alternatively, the orifices may be arranged in inhomogeneous distribution in the distributor plate. The distributor plate may be configured such that the ratio of the sum total of the cross-sectional areas of the orifices to a surface area of the distributor plate is from 0.1 to 0.4, preferably from 0.2 to 0.3 and even more preferably from 0.2 to 0.25, for example 0.225. The feed orifice for supply of a hydrocarbonaceous stream may be arranged essentially radially with respect to a center axis of the mixing section. The feed orifice for supply of an oxygenous stream may be arranged essentially parallel to a center axis of the mixing section. The mixing section may be connected to a mixing tube having a length and a diameter, the length and diameter being configured such that a mixture of the oxygenous stream and the hydrocarbonaceous stream in operation of the apparatus for preparing acetylene and synthesis gas by partial oxidation of hydrocarbons with oxygen in the mixing tube has a flow velocity of 0.2 mach to 1 mach, preferably of 0.3 mach to 0.9 mach and even more preferably of 0.4 mach to 0.8 mach, for example 0.6 mach. The swirl register may have a swirl number of 0.3 to 1, preferably of 0.5 to 0.7 and even more preferably of 0.55 to 0.65, for example 0.6. In other words, a flow that flows through the swirl register has a flow state with such a swirl number.

A process according to the invention for preparing acetylene and synthesis gas by partial oxidation of hydrocarbons with oxygen comprises a mixing unit, a mixing section and a mixing diffuser. A hydrocarbonaceous stream is fed to the mixing section through a feed orifice. An oxygenous stream is fed to the mixing section through a feed orifice. A distributor plate is disposed between the mixing section and the feed orifice for supply of a hydrocarbonaceous stream. The distributor plate has orifices. The swirl register is disposed between the feed orifice for supply of an oxygenous stream and the mixing section. A mixing diffuser is connected to the mixing section.

The distributor plate may be configured such that the ratio of the sum total of the cross-sectional areas of the orifices to a surface area of the distributor plate is from 0.1 to 0.4, preferably from 0.2 to 0.3 and even more preferably from 0.2 to 0.25, for example 0.225. The hydrocarbonaceous stream can be fed in essentially radially with respect to a center axis of the mixing section. The oxygenous stream can be fed in essentially parallel to a center axis of the mixing section. The mixing tube may have a length and a diameter, the length and diameter being configured such that the process for preparing acetylene and synthesis gas by partial oxidation of hydrocarbons with oxygen is conducted in such a way that a mixture of the oxygenous stream and the hydrocarbonaceous stream in the mixing tube has a flow velocity of 0.2 mach to 1 mach, preferably of 0.3 mach to 0.9 mach and even more preferably of 0.4 mach to 0.8 mach, for example 0.6 mach. The swirl register may have a swirl number of 0.3 to 1, preferably of 0.5 to 0.7 and even more preferably of 0.55 to 0.65, for example 0.6.

In the context of the present invention, a mixing unit of a reactor is understood to mean that region of the reactor in which the separately heated starting materials, for example natural gas and oxygen, are combined and begin to mix. The mixing operation takes place in a mixing section.

In the context of the present invention, a mixing tube is understood to mean a tubular component in which the separately heated and already combined starting materials are mixed vigorously. Since the starting materials in the mixing tube have a high flow velocity of 0.2 mach to 1 mach, they are distributed or mixed rapidly.

In the context of the present invention, a mixing diffuser is understood to be a component which slows gas and/or liquid flows and homogenizes the mixture and flow velocities. In the context of the present invention, this is achieved by an increase in the flow cross section in flow direction of the flowing medium.

In the context of the present invention, a distributor plate is understood to mean a component in the form of a plate for distribution of the hydrocarbonaceous stream over the mixing section. The distributor plate need not be flat or planar, but may, for example, be cylindrical. The distributor plate has orifices. The orifices are configured for distribution of the hydrocarbonaceous stream over the mixing section, in that the hydrocarbonaceous stream passes through the orifices into the mixing section. Since the orifices are distributed over the plate, the hydrocarbonaceous stream is distributed over the mixing section.

In the context of the present invention, a swirl register is understood to mean a component which imparts a swirl to the oxygenous stream, so as to form a swirl flow. The swirl can be generated, for example, by means of deflecting plates which deflect the oxygenous stream as it flows over them. Swirl flows may be characterized not only by their general flow state, for example laminar or turbulent, but more specifically via the swirl number. The swirl number is the ratio of axial and rotational momentum of a flow. In this context, the angular momentum is weighted with a characteristic length dimension of the flow, for example the outer radius of the flow boundary which is defined by a flow component. Through the measurement of the velocity profile of tangential and axial velocities, it is thus possible to determine the swirl number. It is generally the case that the higher the peripheral components of the velocity field compared to the axial velocities of the swirl flow, the higher the swirl number.

A further possible characteristic for the flow state used in the context of the present invention is the Reynolds number. The Reynolds number is a dimensionless characteristic. It is the ratio of inertial forces to viscous forces. In the case of pipe flows, characteristic parameters used are typically the internal diameter, the magnitude of the velocity averaged over the cross section, and the viscosity of the fluid. The ratio of the product of the averaged velocity with the internal diameter to the viscosity gives the Reynolds number. Below a critical Reynolds number of about 2300 the flow is generally laminar, and above that generally turbulent.

In the context of the present invention, a burner block of a reactor is understood to mean that region of the reactor through which the heated and mixed starting materials flow. The mixed starting materials flow in channels or holes.

Unless stated otherwise, in the context of the present invention, the expressions "channel" and "hole" are used synonymously. In the context of the present invention, a hole is understood to mean a round or non-round breach in a component.

In the context of the present invention, a firing space of a reactor is understood to mean that region of the reactor into which the heated and mixed starting materials pass after flowing through the burner block and are exothermically reacted. Since, in the context of the present invention, the starting materials used are hydrocarbon and oxygen, this exothermic reaction forms mainly acetylene. By-products formed are hydrogen, carbon monoxide and, to a small extent, soot.

In the context of the present invention, a cross-sectional area is understood to mean the surface area of the area exposed in a cross section. This cross section runs at right angles to a center line of that component whose cross-sectional area is being referred to. For example, the cross-sectional area of an orifice is that surface area which can be found in the case of a cross section at right angles to a theoretical center line through the center of the orifice.

In the context of the present invention, a regular pattern is understood to mean a pattern consisting of various elements in a predetermined symmetric or homogeneous order. In other words, the elements are arranged repeatedly at fixed spatial distances from one another.

In the context of the present invention, the expression "essentially" is understood to mean a deviation of not more than 20° or 20% and preferably not more than 15° or 15% from an exact alignment. For example, essentially radial with respect to a center axis means a deviation from an exactly radial direction of not more than 20° and preferably not more than 15°. Analogously, for example, essentially parallel with respect to a center axis means a deviation from an exactly parallel alignment of not more than 20° and preferably not more than 15°. In the specification of a shape of a component, for example essentially cylindrical, "essentially" means that the shape deviates from the ideal shape by not more than 20% and preferably not more than 15%, the percentage relating to a surface of the component.

Further optional details and features of the present invention are apparent from the description which follows of preferred working examples, which are shown schematically in the drawings.

The drawings show:

FIG. 1 a section view of an apparatus for preparing acetylene and synthesis gas

Figure 2:
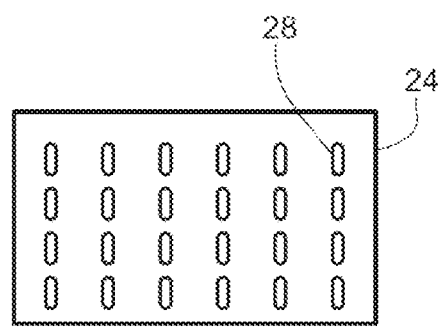

FIG. 2 a diagram of a distributor plate in a theoretical unrolled state and

Figure 3:
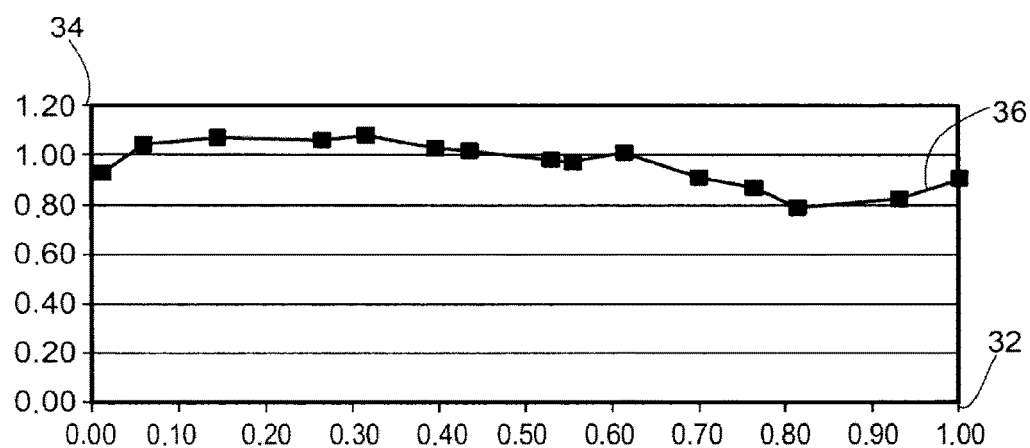

FIG. 3 a simulation result for the simulation of a ratio of a local velocity to a mean velocity over the circumference of the mixing tube.

EMBODIMENTS OF THE INVENTION

FIG. 1 shows a perspective section view of an inventive apparatus for preparing acetylene and synthesis gas by partial oxidation of hydrocarbons with oxygen. The apparatus 10 comprises a mixing unit 12, a mixing section 14 and a mixing diffuser 16. The mixing unit 12 has a feed orifice 18 for supply of a hydrocarbonaceous stream, for example natural gas, a feed orifice 20 for supply of an oxygenous stream, a swirl register 22 and a distributor plate 24. The mixing section 14 adjoins the swirl register 22.

The mixing section 14 is connected to the mixing diffuser 16. The mixing section 14 is essentially cylindrical and has a center axis 26. The feed orifice 18 for supply of a hydrocarbonaceous stream is arranged essentially radially with respect to the center axis 26 of the mixing section 14. The feed orifice 20 for supply of an oxygenous stream is arranged essentially parallel to the center axis 26 of the mixing section 14. The distributor plate 24 is disposed between the mixing section 14 and the feed orifice 18 for supply of a hydrocarbonaceous stream. The distributor plate 24 completely surrounds the mixing section 14, viewed in a circumferential direction about the center axis 26.

FIG. 2 shows a diagram of the distributor plate 24 in a theoretical unrolled state. The distributor plate 24 has orifices 28 for distribution of the hydrocarbonaceous stream. The orifices 28 are preferably arranged in homogeneous distribution in the distributor plate 24. The orifices 28 are introduced into the distributor plate 24, for example, by milling. The orifices 28 are, for example, in the form of elongated holes or ovals. The longer half-axis of any such shape of the orifices 28 may be arranged, for example, parallel to a height of the distributor plate and hence at right angles to the peripheral direction of the distributor plate 24 about the center axis 26. Alternatively, the orifices 28 may be arranged in inhomogeneous distribution in the distributor plate 24. The distributor plate 24 is configured such that the ratio of the sum total of the cross-sectional areas of the orifices 28 to a surface area of the distributor plate 24 is from 0.1 to 0.4, preferably from 0.2 to 0.3 and even more preferably from 0.2 to 0.25, for example 0.225.

The swirl register 22 is disposed between the feed orifice 20 for supply of an oxygenous stream and the mixing section 14. The mixing section 14 thus adjoins the swirl register 22. The swirl register 22 is disposed at least partly within the distributor plate 24. In order to impart a swirl to the oxygenous stream, the swirl register 22 has deflecting plates which are not shown in detail. The swirl register 22 points a swirl number of 0.3 to 1, preferably of 0.5 to 0.7 and even more preferably of 0.55 to 0.65 have, for example 0.6.

As mentioned above, the mixing section 14 is connected to the mixing diffuser 16. More specifically, the mixing section 14 is connected to a mixing tube 30 which is in turn connected to the mixing diffuser 16. The mixing diffuser 16 may have a half opening angle α of less than 8°, preferably less than 4° and even more preferably less than 2°, for example 1.5°. The mixing tube 30 has a length and a diameter. The length and diameter are configured or fixed such that a mixture of the oxygenous stream and the hydrocarbonaceous stream, in operation of the apparatus 10 for preparing acetylene and synthesis gas by partial oxidation of hydrocarbons with oxygen, in the mixing tube 30, has a flow velocity of 0.2 mach to 1 mach, preferably of 0.3 mach to 0.9 mach and even more preferably of 0.4 mach to 0.8 mach, for example 0.6 mach.

There follows a description of a process according to the invention for preparing acetylene and synthesis gas by partial oxidation of hydrocarbons with oxygen, which can be used in the case of the apparatus 10. The hydrocarbons, for example natural gas, and the oxygen are preheated separately as starting gases and provided as separate streams. A hydrocarbonaceous stream is fed to the mixing section 14 through the feed orifice 18. Because of the particular above-described arrangement of the feed orifice 18, the hydrocarbonaceous stream is fed in essentially radially with respect to the center axis 26 of the mixing section 14. An oxygenous stream is fed to the mixing section 14 through the feed orifice 20. Because of the particular above-described arrangement of the feed orifice 20, the oxygenous stream is fed in essentially axially or in parallel with respect to the center axis 26 of the mixing section 14. The hydrocarbonaceous stream penetrates the distributor plate 24 through the orifices 28 and is thus distributed homogeneously into the mixing section 14. In the mixing section 14, the hydrocarbonaceous stream mixes vigorously with the oxygenous stream which is fed to the mixing section 14 through the feed orifice 20. The oxygenous stream fed in is twisted or swirled in the swirl register 22 by means of the deflecting plates and thus ensures better mixing with the hydrocarbonaceous stream in the mixing section 14. The swirl register 22 points a swirl number of 0.3 to 1, preferably of 0.5 to 0.7 and even more preferably of 0.55 to 0.65 have, for example 0.6. In other words, the deflecting plates of the swirl register 22 ensure that the oxygenous stream has a flow state with the swirl numbers mentioned.

The mixture of the hydrocarbonaceous stream and the oxygenous stream then passes into the mixing tube 30. Because of the above-described particular ratio of length and diameter of the mixing tube 30, the mixture of the hydrocarbonaceous stream and the oxygenous stream in the mixing tube 30 has a flow velocity of 0.2 mach to 1 mach, preferably of 0.3 mach to 0.9 mach and even more preferably of 0.4 mach to 0.8 mach, for example 0.6 mach. This high flow velocity ensures further rapid and effective distribution or mixing of the hydrocarbonaceous stream and the oxygenous stream.

From the mixing tube 30, the mixture of the hydrocarbonaceous stream and the oxygenous stream passes into the mixing diffuser 16. In the mixing diffuser 16, the mixture of the hydrocarbonaceous stream and the oxygenous stream, because of the above-described widening of the cross section of the mixing diffuser 16, viewed in flow direction, experiences a reduction in flow velocity and an increase in dynamic pressure. From the mixing diffuser 16, the mixture of the hydrocarbonaceous stream and the oxygenous stream then ultimately arrives at the burner block with the firing space. In the firing space, the mixture of the hydrocarbonaceous stream and the oxygenous stream is reacted for preparation of acetylene and then cooled rapidly by a quench unit.

FIG. 3 shows a simulation result for a simulation of a local velocity over the circumference of the mixing tube 30 relative to a mean velocity. The x axis 32 shows the relative position based on the circumferential direction of the mixing tube 30, i.e. the position X relative to π×diameter of the mixing tube 30. The y axis 34 shows the ratio of the local velocity to the mean velocity as a dimensionless characteristic. The curve 36 shows the local velocity that exists in the above-described apparatus 10 and the process according to the invention over the circumference of the mixing tube 30 relative to a mean velocity. As can be inferred from the diagram in FIG. 3 on the basis of the curve 36, the ratio of the local velocity to the mean velocity varies only slightly around the value of 1.00. This means that there is a homogeneous velocity distribution over the entire circumference of the mixing tube 30, i.e. the entire cross-sectional area of the mixing tube 30. Accordingly, any possible maldistribution downstream of the swirl register 22 is avoided. The design of the swirl register 22 and of the cross section of the mixing unit 12 can also prevent an unwanted hydrodynamic pressure surge in the mixing unit 12. This can be achieved through the special design of the swirl register 22 and of the distributor plate 24.

LIST OF REFERENCE NUMERALS

10 apparatus
12 mixing unit
14 mixing section
16 mixing diffuser
18 feed orifice for hydrocarbon stream
20 feed orifice for oxygen stream
22 swirl register
24 distributor plate
26 center axis
28 orifices
30 mixing tube
32 X axis
34 Y axis
36 curve
$\alpha$ half opening angle

The invention claimed is:

1. An apparatus, comprising a mixing unit, a mixing section and a mixing diffuser,
   wherein the mixing unit has a feed orifice for supply of a hydrocarbonaceous stream, a feed orifice for supply of an oxygenous stream, a swirl register and a distributor plate,
   wherein the distributor plate is disposed between the mixing section and the feed orifice for supply of a hydrocarbonaceous stream,
   wherein the swirl register is disposed between the feed orifice for supply of an oxygenous stream and the mixing section and the swirl register imparts a swirl flow to the oxygenous stream in the mixing section,
   wherein the distributor plate has orifices such that the hydrocarbonaceous stream passes through the orifices and directly enters the the oxygenous stream in the mixing section, and
   wherein the mixing diffuser is connected to the mixing section.

2. The apparatus according to claim 1, wherein the mixing section is essentially cylindrical, and wherein the distributor plate is configured such that the distributor plate completely surrounds the mixing section, viewed in a circumferential direction.

3. The apparatus according to claim 1, wherein the swirl register is disposed at least partly within the distributor plate.

4. The apparatus according to claim 1, wherein the orifices are arranged in homogeneous or inhomogeneous distribution in the distributor plate.

5. The apparatus according to claim 4, wherein the distributor plate is configured such that the ratio of the sum total of the cross-sectional areas of the orifices to a surface area of the distributor plate is from 0.1 to 0.4.

6. The apparatus according to claim 1, wherein the feed orifice for supply of the hydrocarbonaceous stream is arranged essentially radially with respect to a center axis of the mixing section.

7. The apparatus according to claim 1, wherein the feed orifice for supply of an oxygenous stream is arranged essentially parallel to a center axis of the mixing section.

8. The apparatus according to claim 1, wherein the mixing section is connected to a mixing tube having a length and a diameter, wherein the length and diameter are configured such that a mixture of the oxygenous stream and the hydrocarbonaceous stream in operation of the apparatus in the mixing tube has a flow velocity of 0.2 mach to 1 mach.

9. The apparatus according to claim 1, wherein the swirl register has a swirl number of 0.3 to 1.

10. A process for preparing acetylene and synthesis gas by partial oxidation of hydrocarbons with oxygen in the apparatus of claim 1,
    the method comprising:
    feeding a hydrocarbonaceous stream is to a mixing section through a first feed orifice; and
    feeding an oxygenous stream to the mixing section through a second feed orifice,
    wherein a distributor plate is arranged between the mixing section (14) and the first feed orifice for supply of a hydrocarbonaceous stream,
    wherein the distributor plate has orifices,
    wherein a swirl register is disposed between the second feed orifice for supply of an oxygenous stream and the mixing section, wherein a mixing diffuser is connected to the mixing section.

11. The process according to claim 10, wherein the distributor plate is configured such that the ratio of the sum total of the cross-sectional areas of the orifices to a surface area of the distributor plate is from 0.1 to 0.4.

12. The process according to claim 10, wherein the hydrocarbonaceous stream is fed in essentially radially with respect to a center axis of the mixing section, wherein the oxygenous stream is fed in essentially parallel to a center axis of the mixing section.

13. The process according to claim 10, wherein the mixing tube has a length and a diameter, the length and diameter being configured such that the process for preparing acetylene and synthesis gas by partial oxidation of hydrocarbons with oxygen is conducted such that a mixture of the oxygenous stream and the hydrocarbonaceous stream in the mixing tube has a flow velocity of 0.2 mach to 1 mach.

14. The process according to claim 10, wherein the swirl register has a swirl number of 0.3 to 1.

\* \* \* \* \*